(12) United States Patent
Kipp et al.

(10) Patent No.: US 7,776,360 B2
(45) Date of Patent: Aug. 17, 2010

(54) (POLYALKOXY)SULFONATE SURFACE MODIFIERS

(75) Inventors: James E. Kipp, Wauconda, IL (US); Ton That Hai, Round Lake, IL (US); Bennett P. Melnick, Chicago, IL (US)

(73) Assignees: Baxter International, Deerfield, IL (US); Baxter Healthcare S.A., Wallisellen (CH)

( * ) Notice: Subject to any disclaimer, the term of this patent is extended or adjusted under 35 U.S.C. 154(b) by 326 days.

(21) Appl. No.: 11/304,421

(22) Filed: Dec. 15, 2005

(65) Prior Publication Data

US 2006/0141048 A1 Jun. 29, 2006

Related U.S. Application Data

(60) Provisional application No. 60/638,067, filed on Dec. 21, 2004.

(51) Int. Cl.
*A61K 9/14* (2006.01)
(52) U.S. Cl. ...................................... 424/489
(58) Field of Classification Search ................ 424/489
See application file for complete search history.

(56) References Cited

U.S. PATENT DOCUMENTS

| | | | | |
|---|---|---|---|---|
| 5,183,830 | A | * | 2/1993 | Mohring et al. ............. 521/107 |
| 5,565,188 | A | | 10/1996 | Wong et al. |
| 5,569,448 | A | | 10/1996 | Wong et al. |
| 5,607,813 | A | * | 3/1997 | Uytterhoeven et al. ....... 430/252 |
| 5,718,919 | A | * | 2/1998 | Ruddy et al. ................ 424/489 |
| 5,739,212 | A | * | 4/1998 | Wutz et al. .................. 525/411 |
| 6,264,922 | B1 | * | 7/2001 | Wood et al. .................... 424/45 |

FOREIGN PATENT DOCUMENTS

| | | | |
|---|---|---|---|
| DE | 42 02 187 | * | 7/1993 |
| JP | 46043988 | * | 12/1971 |

OTHER PUBLICATIONS

Yanic et al., Adsorbed surfactants for affinity chromatography: end-group modification of ethylene glycol polymers, Bioorganic & Medicinal Chemistry Letters (2003), 13(7), 1381-1384.*

Alexandridis et al, "Poly(ethylene oxide)-poly( propylene oxide)-poly(ethylene oxide) block copolymer surfactants in aqueous solutions and at interfaces: thermodynamics,structure,dynamics and modeling". Colloids and Surfaces: A: Physicochemical and Engineering Aspects, 1995, vol. 96, pp. 1-46.
Dyer et al, "Development of a Chronic Toxicity Structure-Activity Relationship for Alkyl Sulfates". Environmental Toxicology and Water Quality, 1997, vol. 12, pp. 295-303.
Lai et al, "Synthesis and Properties of Water-Soluble bis-paracyclophanes". Tetrahedron Letters, 1985, vol. 26, pp. 5179-5182.
Lee et al, "Particle Size Reduction". In: Water-Insoluble Drug Formulation (Ed. R. Liu) Sep. 2000., CRC Press pp. 455-492.
Rist et al, "Synthesis of new geminal surfactants". Synthetic Communications, 1999, vol. 29, pp. 749-754.
International Search Report, PCT/US2005/045321, Jul. 24, 2006, pp. 1-6.
Written Opinion of International Searching Authority, PCT/US2005/045321, Jul. 24, 2006, pp. 1-6.

* cited by examiner

*Primary Examiner*—Sikarl A Witherspoon
*Assistant Examiner*—Chukwuma O Nwaonicha
(74) *Attorney, Agent, or Firm*—Marshall, Gerstein & Borun LLP (57) ABSTRACT

The present invention is directed to novel compounds, methods of manufacture and methods of use. The present invention is also directed to solid drug/active agent particles having one or more of the compounds of the present invention associated with the surface thereof.

The compounds of the present invention are comprised of a non-polar polyether covalently linked to an anionic sulfonate group. The compounds have an amphipathic quality and preferably, are surface active. Such compounds are preferably useful as surface-active agents to coat and stabilize dispersions of particles in a continuous liquid medium. These surface-active agents may be applied in the stabilization of suspensions, emulsions, or liposome formulations intended for pharmaceutical, medical, cosmetic, or agricultural use.

The particles that can be prepared by a variety of methods and will preferably comprise a pharmaceutical agent. Pharmaceutical compositions of the present invention can be used to treat a myriad of conditions and can be administered by many routes, including intravenous, intramuscular, subcutaneous, intrathecal, subdural, intracameral, intracerebral, intralesional, topical, oral, buccal, rectal, transcutaneous, pulmonary, and nasal.

27 Claims, 3 Drawing Sheets

Figure 1: Particle size distribution of nanosuspension as prepared in Example 3. Values determined by static light scattering (Horiba).

Figure 2: Particle size distribution (static light scattering, measured by Horiba HA-920) before and after autoclave (1% nanosuspension prepared using 0.1% poloxamer 188 and 0.1% sodium deoxycholate).

Figure 3: Particle size distribution (static light scattering, measured by Horiba HA-920) before and after autoclave (1% nanosuspension prepared using 0.1% poloxamer 188, bis(4-butanesulfonic acid, sodium)).

(POLYALKOXY)SULFONATE SURFACE MODIFIERS

This application claims priority to U.S. Provisional Patent Application No. 60/638,067, filed Dec. 21, 2004.

BACKGROUND OF THE INVENTION

1. Technical Field

The present invention relates to a novel class of compounds, methods of synthesis and uses thereof. The present invention also relates to solid drug/active agent nanoparticles having compounds of the present invention associated with the surface thereof.

2. Background Art

The long-term stabilization of nanosuspensions is an uphill battle against the thermodynamics of a metastable, dispersed system. Given enough time, all suspensions will eventually coalesce. Stability therefore rests on the ability to kinetically impede this process. Instability can result from a shift in size distribution to larger particles (Ostwald ripening), irreversible agglomeration, secondary and polymorphic nucleation. In order to obtain a stable suspension, the considerable potential energy created by the large interface between the solid and the surrounding medium must be reduced by adding surface-active agents. Surface stabilization may be achieved by using charged amphiphiles that migrate to the solid-liquid interface and provide an electrostatic barrier to particle agglomeration. Non-ionic polymers may also aid in surface stabilization. Polymeric surfactants such as poloxamer 188, a triblock co-polymer of ethylene glycol and propylene glycol, are very effective non-ionic stabilizers because of multiple attachments of hydrophobic domains at the particle surface.

Entropically, the probability of detachment of all of these hydrophobic moieties is very low at room temperature, thus providing a strong surface affinity (Alexandridis, P.; Hatton, T. A., *Poly(ethylene oxide)-poly(propylene oxide)-poly(ethylene oxide) block copolymer surfactants in aqueous solutions and at interfaces: thermodynamics, structure, dynamics, and modeling (Review)* in *Colloids and Surfaces A: Physicochem. Eng. Aspects*, volume 96, pages 1-46, (1995)). Non-ionic surfactants may also create a hydration zone, a layer of tightly bound water molecules around each particle. When two particles meet, work is required to dislodge this water layer because of osmotic forces. Other entropic factors are also involved. The hydrophobic domains of the surfactant associate with the particle surface, with pendant hydrophilic domains extending into the aqueous medium. Attraction between particles necessitates the intertwining of these pendant chains leading to a restriction in chain mobility, and hence an unfavorable lowering of entropy (Lee, R. W., Shaw, J. M., McShane, J., Wood, R. W.,. *Particle size reduction*. In: Liu, R. (Ed.), *Water-insoluble drug formulation, Interpharm*, p. 478 (2000b.)). This type of stabilization ("steric"), may provide an effective barrier to aggregation. Often, however, a combination of non-ionic and electrostatic stabilization is required to achieve desired particle stability. Glycol copolymers may suffer from reduced solubility in water at high temperatures, which leads to particle aggregation. This results from thermally induced cleavage of hydrogen bonds between the hydrated polymer and water, leading to formation of visible polymer aggregates ("cloud point"). The ability to autoclave such formulations is limited if the cloud point lies below the sterilization temperature (121° C.). Addition of cloud-point modifiers, usually anionic surfactants such as sodium dodecyl sulfate, may raise the cloud point and enhance stability at high temperature (See Lee et al., *Particle size reduction*, pages 487-488.). Polysorbates (Tweens), poloxamines and poloxamers have been used as non-ionic surfactants. Bile salts (e.g., sodium cholate) and alkyl sulfonates (sodium dodecyl sulfate, sodium dioctylsulfosuccinate, and sodium lauryl sulfate, for example) have been effectively used as ionic surfactants.

It is therefore advantageous to provide both a block copolymeric surfactant with multiple hydrophobic domains as well as provide a charged, amphiphilic surfactant (secondary, ionic surfactant) that sets up a surface charge on the particles, thereby preventing interparticle approach because of electrostatic repulsion. One example of a secondary, ionic surfactant is sodium dodecylsulfonate. Another example is dioctyl sulfosuccinate. However, one then relies on non-covalent, van der Waals interactions between the ionic surfactant and the non-ionic, polymeric surfactant. The potential exists for inadequate suspension stability because of incomplete association of the secondary (ionic) surfactant with the primary (nonionic) surfactant, and thus ineffective interaction of the ionic surfactant with the particle surface.

The present invention provides a solution to the problem by the provision of compounds comprising a non-ionic polymer covalently linked to an anionic sulfonate. This novel class of compounds, among other properties, ensures that the anionic portion is always tied to the polymer, which is in turn strongly bound to the particle surface by the entropic and enthalpic forces described above.

Wong, et al. (U.S. Pat. No. 5,565,188, *Polyalkylene block copolymers as surface modifiers for nanoparticles*) discloses a composition containing nanoparticles having a surface modifier wherein the surface modifier is a block copolymer containing one or more polyoxyethylene blocks and one or more polyoxy (higher alkylene) blocks and wherein at least some of the blocks are linked together by a linking group characterized in that the linking group is an oxymethylene group. The present invention compounds are, in contrast to the '188 compounds, sulfonates and are not cross-linked.

Wong, et al. (U.S. Pat. No. 5,569,448, *Sulfated nonionic block copolymer surfactants as stabilizer coatings for nanoparticle compositions*) disclose a composition comprised of nanoparticles containing a therapeutic or diagnostic agent having a surface modifier adsorbed on the surface thereof, wherein said composition is autoclavable and after autoclaving the nanoparticles have an average particle size of less than 500 nm, and wherein the surface modifier is a triblock copolymer having the structure:

where Q is a sulfate group, R is a hydrogen or metal ion, x is 15-700, y is 5-200, and z is 15-700. The polymer backbone is thus a block co-polymer of ethylene glycol and 1,2-butylene glycol. The present invention pendent groups, Q, are sulfonate, not sulfate as those disclosed in the '448 patent. Organic sulfates demonstrate a completely different chemistry and pharmacology than sulfonates. For example, the sulfates are more chemically reactive (sulfate is a good leaving group in nucleophilic displacement reactions) and more toxic because of the ability of such reagents to potentially act as alkylating agents [(a) Dyer, S. D.; Lauth, J. R.; Moral, S. W.; Herzog, R. R.; Cherry, D. S., *Development of a chronic toxicity structure activity relationship for alkyl sulfates. Environ. Toxic. Chem.*, volume 12, pages 295-303 (1997); and (b)

Druckrey, H.; Kruse, H.; Preussmann, R.; Ivankovic, S.; Landschutz., C., *Carcinogenic alkylating substances, Alkyl halogenides, sulfates, sulfonates and strained heterocyclic compounds*. Z. Krebsforsch., volume 74, pages 241-270 (1970).]. Sulfonate salts, on the other hand, are more stable, nearly chemically inert, and thus less toxic.

SUMMARY OF THE INVENTION

The present invention is directed to novel compounds, methods of manufacture and methods of use. The present invention is also directed to solid drug/active agent particles having one or more of the compounds of the present invention adsorbed on, or in proximity with, the surface thereof.

The compounds of the present invention are comprised of a non-polar polyether covalently linked to an anionic sulfonate group. The compounds have an amphipathic quality and, preferably, are surface active. Such compounds are preferably useful as surface-active agents to coat and stabilize dispersions of particles in a continuous liquid medium. These surface-active agents may be applied in the stabilization of suspensions, emulsions, or liposome formulations intended for pharmaceutical, medical, cosmetic, or agricultural use.

The present invention particles can be prepared by a variety of methods and will preferably comprise a pharmaceutical agent. Pharmaceutical compositions of the present invention can be used to treat a myriad of conditions and can be administered by many routes, including intravenous, intramuscular, subcutaneous, intraperitoneal, intrathecal, subdural, intracameral, intracerebral, intralesional, topical, oral, buccal, rectal, transcutaneous, pulmonary, and nasal.

DETAILED DESCRIPTION OF THE INVENTION

The present invention is susceptible of embodiments in many different forms. Preferred embodiments of the invention are disclosed with the understanding that the present disclosure is to be considered as exemplifications of the principles of the invention and are not intended to limit the broad aspects of the invention to the embodiments illustrated.

The present invention is described herein using several definitions, as set forth below and throughout the application.

"About" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

"Coated," with respect to a surfactant or other excipient of a particulate (e.g., nano- or micro-particulate) composition, refers to the presence of such compound at, or approximately on, the surface of the particle. A particle "coated" with such compound may be partially or fully covered with the compound and such compound may or may not be partially entrained within the particle.

"Friable" refers to particles that are fragile and are more easily broken down into smaller particles.

"Microsuspension" refers to a suspension of microparticles, and "microparticles" refers to particles of active agent having a mean particle size of about 200 nm to about 5 microns, unless otherwise specified.

"Nanosuspension" refers to a suspension of nanoparticles, and "nanoparticles" and "nanoparticulate" refer to particles of active agent having a mean particle size of about 15 nm to about 2 microns, unless otherwise specified. "Particle suspension" refers to a suspension of particles that can be of various size distributions.

As used herein, "particle size" or "size" (with reference to particles) is determined on the basis of volume-weighted average particle size as measured by conventional particle size measuring techniques well known to those skilled in the art. Such techniques include, for example, sedimentation field flow fractionation, photon correlation spectroscopy, light scattering, disk centrifugation, light microscopy or electron microscopy.

"Presuspension" refers to a solid dispersion that may be amorphous, semi-crystalline, or crystalline, and which has not been reduced sufficiently in size to the desired range and/or requires an input of energy to stabilize the solid dispersion.

"Poorly water soluble" means that the water solubility of the compound is less than about 10 mg/ml.

With reference to stable drug particles, "stable" means that particles do not appreciably flocculate or agglomerate or otherwise increase in particle size.

"Therapeutically effective amount" refers to drug dosage amounts that generally provide an ameliorative effect on the dosed subject. It is emphasized that, due to the variability of disease state and individual response, a "therapeutically effective amount" of a composition of the present invention administered to a particular subject in a particular instance will not always be effective in treating the diseases described herein, even though such dosage is deemed a "therapeutically effective amount" by those skilled in the art. It is to be further understood that drug dosages are, in particular instances, measured as parenteral or oral dosages, or with reference to drug levels as measured in either blood or plasma.

The term "alkyl" includes straight or branched chain aliphatic hydrocarbon groups that are saturated, that is, they contain no carbon-carbon double bonds. The alkyl groups may be interrupted by one or more heteroatoms, such as oxygen, nitrogen, or sulfur, and may be substituted with other groups, such as halogen, hydroxyl, aryl, cycloalkyl, aryloxy, or alkoxy. Preferred straight or branched alkyl groups include methyl, ethyl, propyl, isopropyl, butyl, sec-butyl, isobutyl, and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, aryl, aryloxy, alkoxy, or alkyl. Preferred cycloalkyl groups include cyclopropyl, cyclobutyl, cyclopentyl, cyclohexyl, and cycloheptyl.

The term "aryl" refers to carbon-based rings which are aromatic. The rings may be isolated, such as phenyl, or fused, such as naphthyl. The ring hydrogens may be substituted with other groups, such as alkyl, halogen, free or functonalized hydroxy, trihalomethyl, etc.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as alkyl or halogen. Examples of heteroaryl groups include imidazole, pyridine, indole, quinoline, furan, thiophene, benzothiophene, pyrrole, pyrazole, oxazole, isoxazole, thiazole, tetrahydroquinoline, benzofuran, dihydrobenzofuran, and dihydrobenzindole.

The terms "aryloxy", "heteroaryloxy", "alkoxy", "cycloalkoxy", "heterocycloalkoxy", "alkenyloxy", "cycloalkenyloxy", "heterocycloalkenyloxy", and "alkynyloxy" represent an aryl, heteroaryl, alkyl, cycloalkyl, heterocycloalkyl, alkenyl, cycloalkenyl, heterocycloalkenyl, or alkynyl group, respectively, attached through an oxygen linkage.

Other chemical moieties not delineated by the above definitions have meanings customary to those skilled in the art of organic chemistry.

The compounds of the present invention are of the genus described in Formulas 1:

Formula 1 wherein,
x is an integer from 1 to 300, preferably from 3 to 100;
y is an integer from 0 to 300, preferably from 3 to 100;
z in an integer from 0 to 300, preferably from 3 to 100;
$R_A$ and $R_B$ are, independently, a hydrogen atom (H), or a sulfonate of the following formula:

wherein R is an alkyl, cycloalkyl or aryl bridging group, and wherein $R_7$ is either hydrogen (the sulfonic acid can exist as a neutral species, —$SO_3H$), absent (the sulfonic acid can exist as a monoanion, —$SO_3^-$), or a mixture of any these two species in equilibrium; provided, at least one of $R_A$ and $R_B$ is a sulfonic acid group, (defined above); and $R_1$, $R_2$, $R_3$ $R_4$, $R_5$, and $R_6$ are, independently, hydrogen, alkyl, or aryl groups; and salts thereof.

Salt compounds of the present invention include any anionic species of Formula 1 and a cation. Preferred cations include sodium and potassium.

Compounds of the present invention are preferably those wherein x is from 50-150, y is from 20-80 and z is from 50-150; and more preferably wherein x is from 50-110, y is from 20-60 and z is from 50-110; and most preferably wherein x is 80, y is 27 and z is 80 (i.e., poloxamer 188 backbone) or wherein x is 101, y is 56 and z is 101 (i.e., poloxamer 407 backbone).

Preferred alkyl groups include methyl, ethyl, propyl, butyl, sec-butyl, isobutyl, pentyl, hexyl, and the like. Preferred aryl groups include phenyl and substituted phenyl. Preferred aryl groups may also be covalently attached to alkyl groups by covalent binding to any carbon atom of the alkyl moiety, e.g., benzyl, 1-phenylethyl, 2-phenylethyl, and the like. In addition, preferred aryl groups may have alkyl substituents bound to any ring carbon, e.g., 2-methylphenyl, 3-ethylphenyl, 4-(1-methylethyl)phenyl substituents, and the like.

Preferred compounds of the present invention are those wherein propylene and ethylene glycol copolymers are bound through terminal hydroxy oxygens to sulfonate moieties. Preferred compounds of this class include a polymer comprised of a triblock copolymer backbone of ethylene glycol and propylene glycol (i.e., $R_1$, $R_2$, $R_3$ $R_5$, and $R_6$ are hydrogen and $R_4$ is $CH_3$, a "poloxamer") bound covalently to at least one sulfonate (preferably, n-butylsulfonic acid) via a terminal alcoholic oxygen.

A preferred species of compounds of the present invention are those of Formula 2

Formula 2 x is from 50-150, y is from 20-80 and z is from 50-150; more preferably wherein x is from 50-110, y is from 20-60 and z is from 50-110; and most preferably wherein x is 80, y is 27 and z is 80 or wherein x is 101, y is 56 and z is 101.

A more preferred species of compounds of the present invention are those of Formula 3:

Formula 3 x is from 50-150, y is from 20-80 and z is from 50-150; more preferably wherein x is from 50-110, y is from 20-60 and z is from 50-110; and most preferably wherein x is 80, y is 27 and z is 80 or wherein x is 101, y is 56 and z is 101; and wherein R and R' are, independently, absent (i.e., the OR or OR' group is an oxygen anion), hydrogen or the OR or OR' group forms a salt, preferably a sodium salt, or mixtures thereof.

The compounds described in Formulas 1 are amphipathic and, preferably, surface active. Such compounds are preferably useful as surface-active agents to coat and stabilize dispersions of particles in a continuous liquid medium. These surface-active agents may be applied in the stabilization of suspensions, emulsions, or liposome formulations intended for pharmaceutical, medical, cosmetic, or agricultural use.

The (polyalkoxy)sulfonates of the present invention may be synthesized by reaction of the parent polyalkylene glycol (e.g., ethylene, propylene, or block copolymer thereof) with any of the following reagents: (1) sultones (e.g., propyl, butyl, etc.), of the formula shown in Formula 2, where n is an integer from 1 to 6; or (2) substituted alkylsulfonic acids and their salts, such acids exemplified by 2-bromoethylsulfonic acid, 2-chloroethylsulfonic acid, 2-iodoethylsulfonic acid, 3-bromopropylsulfonic acid, 3-chloropropylsulfonic acid, 3-iodopropylsulfonic acid, higher molecular weight analogs of Formula 3, where n is an integer 1 through 20, and X is a substituent group of either the halogen series, Cl, Br, and I, or the sulfonate series consisting of mesylate, tosylate and triflate.

Formula 2

X—CH$_2$(CH$_2$)$_n$SO$_3$H

Formula 3

The following example further illustrate the invention:

EXAMPLE 1

Preparation of Poloxamer 188, Bis(4-Butanesulfonic Acid, Sodium Salt)

Following Scheme 1, below, to a solution of Poloxamer 188 (4.2 g, 0.5 mmol) in toluene (5 mL) at 35-40° C. under argon was added a slurry of sodium methoxide (330 mg, 6.1 mmol) in methanol (2.5 mL). The slurry had been prepared under argon, and addition was made by means of a gas-tight syringe through a septum in the neck of the flask. The mixture was stirred, and the solvents were removed by distillation, collecting approximately 3.5 to 4 mL. The mixture became a light brown paste. 1,4-Butane sultone (0.70 mL, 6.8 mmol) and toluene (2.5 mL) were added, and the mixture was refluxed at 150° C. under argon for 1.5 hours. The oil bath was removed, and the mixture was allowed to stand under argon at room temperature overnight, yielding the crude product as a light brown wax. Thin layer chromatography using methylene chloride/methanol/aqueous ammonia (10:2:0.2, v/v/v) and Silica Gel 60 F254 pre-coated plates (2.5×7.5 cm×250 µm) indicated that nearly complete conversion of starting material to a single product had occurred. The wax was taken up in chloroform (250 mL), yielding a somewhat hazy suspension. A 15-mL aliquot was removed, and the remainder was rotary evaporated to dryness. The residue was further dried in a vacuum oven at 30° C. for 4 hours, yielding 2.8 g of a light brown waxy solid.

A portion of the product (1.52 g) was taken up in 8 mL of distilled water, and a small amount of fine white precipitate formed. The solution and precipitate were transferred to a dialysis cassette (Pierce Slide-A-Lyzer® Dialysis Cassette, 3500 molecular weight cut-off, 3-12 mL capacity, product number 66110). The cassette was attached to a buoy (Pierce Slide-A-Lyzer® Buoys, product number 66432), and the cassette assembly was then placed in 4 L of distilled water in a beaker. The water was gently stirred, the beaker was covered with aluminum foil, and the solution was dialyzed overnight. The cassette assembly was removed from the water and dialyzed a second time with a fresh 4-L portion of distilled water for 4 hours. Dialysis was repeated a third time with a fresh 4-L portion of distilled water for 3 hours. The solution was removed from the cassette by a gas-tight syringe and transferred to a pear-shaped flask. It was clear and colorless. It was freeze-dried overnight to yield the product as a hard, white solid, 1.04 g.

NMR data were obtained (CDCl3) on a DRX600 NMR spectrometer (Bruker Biospin, Billerica, Mass.) with a 5 mm 1H{13C,15N} TXI probe operating at 600 MHz (1H υ). For Poloxamer 188, the methylene units adjacent to the terminal hydroxyl groups have a diagnostic 13C-NMR resonance at approximately 61 ppm. This resonance was absent in the 13C-NMR of the product, indicating an absence of the terminal hydroxyl groups. Instead, resonances were observed in the product at 22.04, 28.67 and 51.19 ppm, attributed to the butylsulfonate moiety. None of these were present in the 13C-NMR spectrum of Poloxamer 188. The NMR data for Poloxamer 188 and its bis-4-butanesulfonic acid, sodium salt, are shown below.

NMR data for Poloxamer 188, bis(4-butanesulfonic acid, sodium salt):

1H NMR (CDCl3): δ 1.100, 1.687, 1.859, 2.764, 2.83, 3.366-3.723.

13C NMR (CDCl3): δ 17.41, 17.53, 22.04, 28.67, 51.19, 68.57, 68.66, 69.98-71.05, 72.95, 73.43, 75.00-75.59.

NMR data for Poloxamer 188:

$^1$H NMR (CDCl$_3$): δ 1.053-1.084, 2.603, 2.785, 3.323-3.692.

$^{13}$C NMR (CDCl$_3$): δ 16.64, 16.75, 60.96, 67.80, 67.87, 69.58-70.21, 71.94, 72.19, 72.60, 74.36-74.72.

Scheme 1:
Synthetic route for preparation of poloxamer 188, bis(4-butanesulfonic acid, wherein R is sodium)

-continued

EXAMPLE 2

Hemolytic Potential (Dynamic Extract Test) of Poloxamer 188, Bis(4-Butanesulfonic Acid, Sodium Salt)

In order to evaluate the potential for lysis of blood cells upon injection of a compound of Formula 1 into a mammalian subject, poloxamer 188, bis(4-butanesulfonic acid, sodium salt) (PBBS-188) was mixed with whole blood and the mixed sample examined for hemolysis. The hemolysis test (Dynamic Extract Test) involves preparing approximately a 1:1 mixture of rabbit blood and sample, placing the mixture on a rocking agitator for 1 hour at 37° C. The samples are then centrifuged and hemoglobin (Hb) is quantified in the supernatant. The hemolytic index is calculated as:

$$\text{Hemolytic Index} = 100 \times \frac{\text{Hemoglobin (mg in supernatant)}}{\text{Total blood (mg)}}$$

A rating of 0-2 is regarded as non-hemolytic, 2-10 as slightly hemolytic, 10-20 as moderately hemolytic, 20-40 as markedly hemolytic, and >40 as severely hemolytic. Results of testing are shown in the following table:

| Test Sample | Hemolytic Index (Mean) | Standard Deviation | Osmolarity (mOsM) |
|---|---|---|---|
| 0.9% sodium chloride | 0.71 | 0.28 | 308 |
| 0.1% DSPE-PEG, 0.9% sodium chloride | 1.04 | 0.46 | 289 |
| 0.1% PBBS-188, 9.25% sucrose | 0.17 | 0.1 | 270 |

The results indicate that 0.1% (w/v) of poloxamer 188, bis(4-butanesulfonic acid, sodium salt) is non-hemolytic, having a mean hemolytic index of 0.17 in an osmotic adjusting medium (9.25% sucrose). This result is significantly lower than the index for 0.9% sodium chloride (normal saline), a commonly used intravenous fluid. It is also significantly lower than the hemolytic index for a pegylated lipid dispersed in normal saline (0.1% DSPE-PEG, 0.9% sodium chloride).

This in-vitro result underscores the likely safety of this compound in an actual injectable product.

The compounds of Formula 1 can be applied in pharmaceutical, medical, diagnostic, cosmetic, agricultural and other areas. Pharmaceutical uses include the combination of the compounds of Formula 1 with therapeutic agents or diagnostic agents. Therapeutic agents can be selected from a variety of known pharmaceuticals such as, but are not limited to: analgesics, anesthetics, analeptics, adrenergic agents, adrenergic blocking agents, adrenolytics, adrenocorticoids, adrenomimetics, anticholinergic agents, anticholinesterases, anticonvulsants, alkylating agents, alkaloids, allosteric inhibitors, anabolic steroids, anorexiants, antacids, antidiarrheals, antidotes, antifolics, antipyretics, antirheumatic agents, psychotherapeutic agents, neural blocking agents, anti-inflammatory agents, antihelmintics, antibiotics, anticoagulants, antidepressants, antiepileptics, antifungals, antihistamines, antimuscarinic agents, antimycobacterial agents, antineoplastic agents, antiprotozoal agents, antiviral agents, anxiolytic sedatives, beta-adrenoceptor blocking agents, contrast media, corticosteroids, cough suppressants, diagnostic agents, diagnostic imaging agents, dopaminergics, hemostatics, hematological agents, hypnotics, immuriological agents, muscarinics, parasympathomimetics, prostaglandins, radiopharmaceuticals, sedatives, stimulants, sympathomimetics, vitamins, xanthines, growth factors, hormones, and antiprion agents. Antineoplastic agents can include paclitaxel and its derivative compounds, alkaloids, antimetabolites, enzyme inhibitors, alkylating agents and antibiotics.

Therapeutic agents can also include a biologic. The biologic can be selected from proteins, polypeptides, carbohydrates, polynucleotides, and nucleic acids. The protein can be an antibody selected from polyclonal antibodies and monoclonal antibodies. Protein examples include, but are not limited to, Factor VIII, Factor IX, insulin, human growth hormone, tPA, streptokinase, urokinase, erythropoietin, alpha-1-proteinase inhibitor and specific monoclonal antibodies or Fab fragments, and derivatives thereof.

Diagnostic agents include the x-ray imaging agents and contrast media. Examples of x-ray imaging agents include WIN-8883 (ethyl 3,5-diacetamido-2,4,6-triiodobenzoate) also known as the ethyl ester of diatrazoic acid (EEDA), WIN 67722, i.e., (6-ethoxy-6-oxohexyl-3,5-bis(acetamido)-2,4,6-triiodobenzoate; ethyl-2-(3,5-bis(acetamido)-2,4,6-triiodobenzoyloxy) butyrate (WIN 16318); ethyl diatrizoxyacetate (WIN 12901); ethyl 2-(3,5-bis(acetamido)-2,4,6-triiodobenzoyloxy)propionate (WIN 16923); N-ethyl 2-(3,5-bis(acetamido)-2,4,6-triiodobenzoyloxy acetamide (WIN 65312); isopropyl 2-(3,5-bis(acetamido)-2,4,6-triiodobenzoyloxy) acetamide (WIN 12855); diethyl 2-(3,5-bis(acetamido)-2,4,6-triiodobenzoyloxy malonate (WIN 67721); ethyl 2-(3,5-bis (acetamido)-2,4,6-triiodobenzoyloxy)phenylacetate (WIN 67585); propanedioic acid, [[3,5-bis(acetylamino)-2,4,5-triodobenzoyl]oxy]bis(1-methyl)ester (WIN 68165); and benzoic acid, 3,5-bis(acetylamino)-2,4,6-triodo-4-(ethyl-3-ethoxy-2-butenoate) ester (WIN 68209). Preferred contrast agents include those that are expected to disintegrate relatively rapidly under physiological conditions, thus minimizing any particle associated inflammatory response. Disintegration may result from enzymatic hydrolysis, solubilization of carboxylic acids at physiological pH, or other mechanisms. Thus, poorly soluble iodinated carboxylic acids such as iodipamide, diatrizoic acid, and metrizoic acid, along with hydrolytically labile iodinated species such as WIN 67721, WIN 12901, WIN 68165, and WIN 68209 or others may be preferred.

Other contrast media include, but are not limited to, particulate preparations of magnetic resonance imaging aids such as gadolinium chelates, or other paramagnetic contrast agents. Examples of such compounds are gadopentetate dimeglumine (Magnevist®) and gadoteridol (Prohance®).

A description of classes of therapeutic agents and diagnostic agents and a listing of species within each class can be found in Martindale, The Extra Pharmacopoeia, Twenty-ninth Edition, The Pharmaceutical Press, London, 1989 which is incorporated herein by reference and made a part hereof. The therapeutic agents and diagnostic agents are commercially available and/or can be prepared by techniques known in the art.

When the protein or other macromolecule compositions of the present invention are formulated, they will generally comprise the protein or other macromolecule and one or more compounds of Formula 1 in an aqueous medium. Such compositions will be in either solution or colloidal form. The compounds of Formula 1 will be present in an amount effective to stabilize the composition. "Stabilize," in this context, refers to the inhibition or partial inhibition of protein/macromolecule denaturation, irregular folding or aggregation, relative to a composition of such molecules, but without one or more compounds of Formula 1.

When particles of the present invention are made, they preferably comprise a pharmaceutical agent that is poorly water-soluble and one or more compounds of Formula 1. What is meant by "poorly water soluble" is a solubility of the compound in water of less than about 10 mg/mL, and preferably less than 1 mg/mL. These poorly water-soluble compounds are most suitable for aqueous suspension preparations since there are limited alternatives of formulating these compounds in an aqueous medium. The particles of the present invention typically will be comprised of a solid crystalline, semi-crystalline, amorphous or mixture forms thereof, of a pharmaceutical agent (or other agent) having one or more compounds of Formula 1 and, optionally one or more surfactants (described below), associated with the surface thereof.

The concentration of compounds of Formula 1 in compositions of the present invention will vary, depending on the particular compound(s) of Formula 1 used, the presence of additional surfactant(s), the phyisical/chemical nature of the pharmaceutical/active agent particle, the particle size and the concentration of the particle in the suspension. In general, however, the compounds of Formula 1 will be present in the particle compositions of the present invention in a concentration of from about 0.01 percent weight to volume (% w/v) to about 5% w/v. Preferably, the compounds of Formula 1 will be present in compositions of the present invention in an amount of from about 0.01-2% w/v and most preferably from about 0.05 to 1% w/v.

The concentration of the pharmaceutical or other active agent will be present in particle form in suspensions of the present invention will vary, depending on the nature of the chemical/physical nature of the agent, the route of administration and administration rate, the condition to treat and so on. In general, however, the active agent will be present in a composition of the present invention in a concentration of from about 0.01 to about 30% w/v, and more preferably from about 0.1 to about 25% w/v, and most preferably about 0.5 to about 20% w/v.

The particles utilized in the present invention have an average effective particle size of less than about 100 µm as measured by dynamic light scattering methods (e.g., photocorrelation spectroscopy, laser diffraction, low-angle laser light scattering (LALLS), medium-angle laser light scattering (MALLS)), light obscuration methods (Coulter method, for example), rheology, or microscopy (light or electron). The preferred average effective particle size depends on factors such as the intended route of administration, formulation, solubility, toxicity and bioavailability of the compound. Preferably, the particles of the present invention will have an average effective particle size of from about 15 nm to 200 µm, more preferably, of from about 15 nm to about 100 µm, more preferably, of from about 15 nm to about 50 µm, and most preferably, of from about 100 nm to about 50 µm. When the particle compositions of the present invention are intended for intravenous infusion, the particles will have an average effective particle size of from 15 nm to about 2 µm, and more preferably 50 nm to about 1 µm.

The following description of particles also applies to all embodiments of the present invention. The particles in the dispersion can be amorphous, semicrystalline, crystalline, or a combination thereof as determined by suitable analytical methods such as differential scanning calorimetry (DSC) or X-ray diffraction. Prior to administration, the pharmaceutical composition can be homogenized through a homogenization process. The pharmaceutical composition can also be homogenized through a microprecipitation/homogenization process.

The dispersion of the pharmaceutical composition can be sterilized prior to administering. Sterilization can be performed by any medical sterilization process including heat sterilization or sterilization by gamma irradiation. It can also be sterilized by filtration, either directly as a dispersion having particle sizes less than 200 nm, or by sterile filtration of the solutions used in the precipitation process, prior to forming the solid dispersion. Sterilization can also be accomplished by brief application of very high pressure (greater than 2000 atmospheres), or by a combination of high pressure and elevated temperature.

The present invention can be practiced with water-soluble compounds. These water-soluble active compounds are mixed with a polymer (for example, polylactate-polyglycolate copolymer (PLGA), polycyanoacrylate, albumin, starch), or encapsulated in a surrounding vesicle that is impermeable to the pharmaceutical compound. This encapsulating vesicle can be a polymeric coating such as polyacrylate. Further, the small particles prepared from these water-soluble compounds can be modified to improve chemical stability and control the pharmacokinetic properties of the compounds by controlling the release of the compounds from the particles. Examples of water-soluble compounds include, but are not limited to, simple organic compounds, proteins, peptides, nucleotides, oligonucleotides, and carbohydrates.

Preparation of Pharmaceutical Particle Compositions of the Present Invention

The processes for preparing the particles used in the present invention can be accomplished through numerous techniques known to those skilled in the art. A representative, but non-exhaustive, discussion of techniques for preparing particle dispersions of pharmaceutical compositions follows. In the following examples, preferred methods and resulting products are comprised of the active agent particulate and one or more compounds of Formula 1 (i.e., without additional surfactant compounds).

I. Energy Addition Techniques for Forming Small Particle Dispersions

In general, the method of preparing small particle dispersions using energy addition techniques includes the step of adding the pharmaceutically active compound, which sometimes shall be referred to as a drug, in bulk form to a suitable vehicle such as water or aqueous solution containing one or more compounds of Formula 1 and, optionally, one or more surfactants set forth below, or other liquid in which the pharmaceutical compound is not appreciably soluble, to form a first suspension, which shall be referred to as a presuspension. Energy is added to the presuspension to form a particle dispersion that is physically more stable than the presuspension. Energy is added by mechanical grinding (e.g., pearl milling, ball milling, hammer milling, fluid energy milling, jet milling, or wet grinding). Such techniques are disclosed in U.S. Pat. No. 5,145,684, which is incorporated herein by reference and made a part hereof.

Energy addition techniques further include subjecting the presuspension to high shear conditions including cavitation, shearing or impact forces utilizing a microfluidizer. The present invention further contemplates adding energy to the presuspension using a piston gap homogenizer or counter current flow homogenizer such as those disclosed in U.S. Pat. No. 5,091,188 which is incorporated herein by reference and made a part hereof. Suitable piston gap homogenizers are commercially available under the product name EMULSIFLEX by Avestin, and French Pressure Cells sold by Spectronic Instruments. Suitable microfluidizers are available from Microfluidics Corp.

The step of adding energy can also be accomplished using sonication techniques. The step of sonicating can be carried out with any suitable sonication device such as the Branson Model S-450A or Cole-Parmer 500/750 Watt Model. Such devices are well known in the industry. Typically the sonication device has a sonication horn or probe that is inserted into the presuspension to emit sonic energy into the solution. The sonicating device, in a preferred form of the invention, is operated at a frequency of from about 1 kHz to about 90 kHz and more preferably from about 20 kHz to about 40 kHz or any range or combination of ranges therein. The probe sizes can vary and preferably is in distinct sizes such as ½ inch or ¼ inch or the like.

Regardless of the energy addition technique used, the dispersion of small particles must be sterilized prior to use. Sterilization can be accomplished by heat sterilization, gamma irradiation, filtration (either directly as a dispersion having particle sizes under 200 nm, or by sterile filtration of the solutions used in the precipitation process, prior to forming the solid dispersion), and by application of very high pressure (greater than 2000 atmospheres), or by a combination of high pressure and elevated temperature.

II. Precipitation Methods for Preparing Submicron Sized Particle Dispersions

Small particle dispersions can also be prepared by precipitation techniques. The following is a description of examples of precipitation techniques.

Microprecipitation Methods

One example of a microprecipitation method is disclosed in U.S. Pat. No. 5,780,062, which is incorporated herein by reference and made a part hereof. The '062 patent discloses an organic compound precipitation process including: (i) dissolving the organic compound in a water-miscible first solvent; (ii) preparing a solution of one or more compounds of Formula 1 and, optionally, one or more surfactants set forth below in an aqueous second solvent and in which second solvent the organic compound is substantially insoluble; and (iii) mixing the solutions from steps (i) and (ii) so as to cause precipitation of an aggregate of the organic compound and the one or more compounds of Formula 1 and, optionally one or more surfactants.

Another example of a suitable precipitation process is disclosed in U.S. Pat. No. 6,607,784 and co-pending and commonly assigned U.S. Ser. Nos. 09/874,499; 09/874,637; and 10/021,692, which are incorporated herein by reference and made a part hereof. The processes disclosed include the steps of: (1) dissolving an organic compound in a water miscible first organic solvent to create a first solution; (2) mixing the first solution with a second solvent or water to precipitate the organic compound to create a presuspension; and (3) adding energy to the presuspension in the form of high-shear mixing or heat to provide a dispersion of small particles. Optionally, the first organic solvent is removed from the mixture by any suitable means such as centrifugation or filtration methods. Moreover, the continuous phase of the dispersion can be optionally replaced by another continuous phase by removing the first continuous phase using methods such as centrifugation and filtration, adding a second continuous phase and subsequently redispersing the solid material in the second continuous phase. One or more compounds of Formula 1 and, optionally, one or more surfactants set forth below are added to the first organic solvent or the second aqueous solution, or both.

Emulsion Precipitation Methods

One suitable emulsion precipitation technique is disclosed in the co-pending and commonly assigned U.S. Ser. No. 09/964,273, which is incorporated herein by reference and is made a part hereof. In this approach, the process includes the steps of: (1) providing a multiphase system having an organic phase and an aqueous phase, the organic phase having a pharmaceutically active compound therein; and (2) sonicating the system to evaporate a portion of the organic phase to cause precipitation of the compound in the aqueous phase to form a dispersion of small particles. The step of providing a multiphase system includes the steps of: (1) mixing a water immiscible solvent with the pharmaceutically active compound to define an organic solution, (2) preparing an aqueous based solution with one or more compounds of Formula 1 and, optionally, one or more surfactants set forth below, and (3) mixing the organic solution with the aqueous solution to form the multiphase system. The step of mixing the organic phase and the aqueous phase can include the use of piston gap homogenizers, colloidal mills, high speed stirring equipment, extrusion equipment, manual agitation or shaking equipment, microfluidizer, or other equipment or techniques for providing high shear conditions. The crude emulsion will have oil droplets in the water of a size of approximately less than 1 μm in diameter. The crude emulsion is sonicated to define a microemulsion and eventually to provide a dispersion of small particles.

Another approach to preparing a dispersion of small particles is disclosed in co-pending and commonly assigned U.S. Ser. No. 10/183,035, which is incorporated herein by reference and made a part hereof. The process includes the steps of: (1) providing a crude dispersion of a multiphase system having an organic phase and an aqueous phase, the organic phase having a pharmaceutical compound therein; (2) providing energy to the crude dispersion to form a fine dispersion; (3) freezing the fine dispersion; and (4) lyophilizing the fine dispersion to obtain small particles of the pharmaceutical compound. The small particles can be sterilized by the techniques set forth below or the small particles can be reconstituted in an aqueous medium and sterilized.

The step of providing a multiphase system includes the steps of: (1) mixing a water immiscible solvent with the pharmaceutically effective compound to define an organic solution; (2) preparing an aqueous based solution with one or more compounds of Formula 1 and, optionally, one or more surfactants set forth below; and (3) mixing the organic solution with the aqueous solution to form the multiphase system. The step of mixing the organic phase and the aqueous phase includes the use of piston gap homogenizers, colloidal mills, high speed stirring equipment, extrusion equipment, manual agitation or shaking equipment, microfluidizer, or other equipment or techniques for providing high shear conditions.

Solvent-Antisolvent Precipitation

Small particle dispersions can also be prepared using solvent anti-solvent precipitation technique disclosed by Fessi et al. in U.S. Pat. No. 5,118,528 and by Leclef et al. in U.S. Pat. No. 5,100,591 which are incorporated herein by reference and made a part hereof. Both processes include the steps of: (1) preparing a liquid phase of a biologically active substance in a solvent or a mixture of solvents to which may be added one or more compounds of Formula 1 and, optionally, one or more surfactants set forth below; (2) preparing a second liquid phase of a non-solvent or a mixture of non-solvents, the non-solvent is miscible with the solvent or mixture of solvents for the substance; (3) adding together the solutions of (1) and (2) with stirring; and (4) removing of unwanted solvents to produce a dispersion of small particles. These methods are distinguished from those described under the above section, "Microprecipitation Methods," in that they do not provide for a last step of adding energy to the suspension in the form of high-shear mixing or heat.

Phase Inversion Precipitation

Small particle dispersions can be formed using phase inversion precipitation as disclosed in U.S. Pat. Nos. 6,235,224, 6,143,211 and U.S. Patent Application No. 2001/0042932, each of which is incorporated herein by reference and made a part hereof. Phase inversion, as applied to the present invention, employs a physical phenomena by which one or more compounds of Formula 1 and, optionally, one or more surfactants set forth below dissolved in a continuous phase solvent system inverts into a solid macromolecular network in which such compounds are the continuous phase. One method to induce phase inversion is by the addition of a nonsolvent to the continuous phase. The compound(s) of Formula 1 and, optionally, surfactant(s) undergo a transition from a single phase to an unstable two phase mixture: polymer rich and polymer poor fractions. Micellar droplets of nonsolvent in the polymer rich phase serve as nucleation sites and become coated with polymer. The '224 patent discloses that phase inversion of polymer solutions under certain conditions can bring about spontaneous formation of discrete microparticles, including nanoparticles. The '224 patent discloses dissolving or dispersing a polymer in a solvent. A pharmaceutical agent is also dissolved or dispersed in the solvent. For the crystal seeding step to be effective in this process it is desirable the agent is dissolved in the solvent. The polymer, the agent and the solvent together form a mixture having a continuous phase, wherein the solvent is the continuous phase. The mixture is then introduced into at least tenfold excess of a miscible nonsolvent to cause the spontaneous formation of the microencapsulated microparticles of the agent having an average particle size of between 10 nm and 10 µm. The particle size is influenced by the solvent:nonsolvent volume ratio, polymer concentration, the viscosity of the polymer-solvent solution, the molecular weight of the polymer, and the characteristics of the solvent-nonsolvent pair.

pH Shift Precipitation

Small particle dispersions can be formed by pH shift precipitation techniques. Such techniques typically include a step of dissolving a drug in a solution having a pH where the drug is soluble, followed by the step of changing the pH to a point where the drug is no longer soluble. The pH can be acidic or basic, depending on the particular pharmaceutical compound. The solution is then neutralized to form a dispersion of small particles. One suitable pH shifting precipitation process is disclosed in U.S. Pat. No. 5,665,331, which is incorporated herein by reference and made a part hereof. The process includes the step of dissolving of the pharmaceutical agent together with a crystal growth modifier (CGM) in an alkaline solution and then neutralizing the solution with an acid in the presence of suitable surface-modifying surface-active agent of one or more compounds of Formula 1 and, optionally, one or more surfactants set forth below, to form a small particle dispersion of the pharmaceutical agent. The precipitation step can be followed by steps of diafiltration clean-up of the dispersion and then adjusting the concentration of the dispersion to a desired level.

Other examples of pH shifting precipitation methods are disclosed in U.S. Pat. Nos. 5,716,642; 5,662,883; 5,560,932; and 4,608,278, which are incorporated herein by reference and are made a part hereof.

Infusion Precipitation Method

Suitable infusion precipitation techniques to form small particle dispersions are disclosed in the U.S. Pat. Nos. 4,997,454 and 4,826,689, which are incorporated herein by reference and made a part hereof. First, a suitable solid compound is dissolved in a suitable organic solvent to form a solvent mixture. Then, a precipitating nonsolvent miscible with the organic solvent is infused into the solvent mixture at a temperature between about −10° C. and about 100° C. and at an infusion rate of from about 0.01 ml per minute to about 1000 ml per minute per volume of 50 ml to produce a suspension of precipitated non-aggregated solid particles of the compound with a substantially uniform mean diameter of less than 10 µm. Agitation (e.g., by stirring) of the solution being infused with the precipitating nonsolvent is preferred. The nonsolvent contains one or more compounds of Formula 1 and, optionally, one or more surfactants set forth below to stabilize the particles against aggregation. The particles are then separated from the solvent. Depending on the solid compound and the desired particle size, the parameters of temperature, ratio of nonsolvent to solvent, infusion rate, stir rate, and volume can be varied in order to achieve the desired suspension. The particle size is proportional to the ratio of nonsolvent:solvent volumes and the temperature of infusion and is inversely proportional to the infusion rate and the stirring rate. The precipitating nonsolvent may be aqueous or non-aqueous, depending upon the relative solubility of the compound and the desired suspending vehicle.

Temperature Shift Precipitation

Temperature shift precipitation techniques may also be used to form small particle dispersions. This technique is disclosed in U.S. Pat. No. 5,188,837, which is incorporated herein by reference and made a part hereof. In an embodiment of the invention, liospheres are prepared by the steps of: (1) melting or dissolving a substance such as a drug to be delivered in a molten vehicle to form a liquid of the substance to be delivered; (2) adding a phospholipid and one or more compounds of Formula 1 and, optionally, one or more surfactants set forth below, along with an aqueous medium to the melted substance or vehicle at a temperature higher than the melting temperature of the substance or vehicle; (3) mixing the suspension at a temperature above the melting temperature of the vehicle until a homogenous fine preparation is obtained; and then (4) rapidly cooling the preparation to room temperature or below.

Solvent Evaporation Precipitation

Solvent evaporation precipitation techniques are disclosed in U.S. Pat. No. 4,973,465 which is incorporated herein by reference and made a part hereof. The '465 Patent discloses methods for preparing microcrystals including the steps of: (1) providing a solution of a pharmaceutical composition and a phospholipid and one or more compounds of Formula 1 and, optionally, one or more surfactants set forth below, dissolved in a common organic solvent or combination of solvents, (2) evaporating the solvent or solvents and (3) suspending the film obtained by evaporation of the solvent or solvents in an aqueous solution by vigorous stirring to form a dispersion of small particles. The solvent can be removed by evaporating a sufficient quantity of the solvent to cause precipitation of the compound. The solvent can also be removed by other well known techniques such as applying a vacuum to the solution or blowing nitrogen over the solution.

Reaction Precipitation

Reaction precipitation includes the steps of dissolving the pharmaceutical compound, and optionally other excipients, into a suitable solvent to form a solution. The compound may be added in an amount at or below the saturation point of the compound in the solvent. The compound or any of the excipients is precipitated from solution by reacting with a chemical agent or by modification in response to adding energy such as heat or UV light or the like such that the modified compound has a lower solubility in the solvent and precipitates from the solution to form a small particle dispersion. Precipitation of excipient provides a solid matrix into which the drug is sorbed.

Compressed Fluid Precipitation

A suitable technique for precipitating by compressed fluid is disclosed in WO 97/14407 to Johnston, which is incorporated herein by reference and made a part hereof. The method includes the steps of dissolving a water-insoluble drug in a solvent to form a solution. The solution is then sprayed into a compressed fluid, which can be a gas, liquid or supercritical fluid. The addition of the compressed fluid to a solution of a solute in a solvent causes the solute to attain or approach supersaturated state and to precipitate out as fine particles. In this case, the compressed fluid acts as an anti-solvent that lowers the cohesive energy density of the solvent in which the drug is dissolved.

Alternatively, the drug can be dissolved in the compressed fluid, which is then sprayed into an aqueous phase. The rapid expansion of the compressed fluid reduces the solvent power of the fluid, which in turn causes the solute to precipitate out as small particles in the aqueous phase. In this case, the compressed fluid acts as a solvent.

In order to stabilize the particles against aggregation, one or more compounds of Formula 1 and, optionally, one or more surfactants set forth below, is included in this technique.

Spraying into Cryogenic Fluids

A suitable technique for precipitating by compressed fluid is disclosed by Williams et al. in U.S. application Ser. No. 10/273,730, which is incorporated herein by reference and made a part hereof. The method provides a system and method for the production of small particles wherein the active ingredient is mixed with water, one or more solvents, or a combination thereof, and one or more compounds of Formula 1 and, optionally, one or more surfactants set forth below, and the resulting mixture sprayed at or below the surface of a cryogenic fluid. Frozen particles are thereby provided. Materials for encapsulating the solid particles may also be added so that frozen particles are generated wherein the encapsulating agent surrounds the active agent.

III. Additional Methods for Preparing Particle Dispersions of Pharmaceutical Compositions The following additional processes for preparing particles of pharmaceutical compositions (i.e. organic compound) used in the present invention can be separated into four general categories. Each of the categories of processes share the steps of: (1) dissolving an organic compound in a water miscible first solvent to create a first solution, (2) mixing the first solution with a second solvent of water to precipitate the organic compound to create a pre-suspension, and (3) adding energy to the presuspension in the form of high-shear mixing or heat, or a combination of both, to provide a stable form of the organic compound having the desired size ranges defined above. The mixing steps and the adding energy step can be carried out in consecutive steps or simultaneously.

The categories of processes are distinguished based upon the physical properties of the organic compound as determined through x-ray diffraction studies, differential scanning calorimetry DSC studies, or other suitable study conducted prior to the energy-addition step and after the energy-addition step.

A. First Process Category

The methods of the first process category generally include the step of dissolving the organic compound in a water miscible first solvent followed by the step of mixing this solution with an aqueous solvent to form a presuspension wherein the organic compound is in an amorphous form, a semicrystalline form or in a supercooled liquid form as determined by x-ray diffraction studies, DSC, light microscopy or other analytical techniques and has an average effective particle size within one of the effective particle size ranges set forth above. The mixing step is followed by an energy-addition step.

B. Second Process Category

The methods of the second processes category include essentially the same steps as in the steps of the first processes category but differ in the following respect. An x-ray diffraction, DSC or other suitable analytical techniques of the pre-suspension shows the organic compound in a crystalline form and having an average effective particle size. The organic compound after the energy-addition step has essentially the same average effective particle size as prior to the energy-addition step but has less of a tendency to aggregate into larger particles when compared to that of the particles of the presuspension. Without being bound to a theory, it is believed the differences in the particle stability may be due to a reordering of the surfactant molecules at the solid-liquid interface.

C. Third Process Category

The methods of the third category modify the first two steps of those of the first and second processes categories to ensure the organic compound in the presuspension is in a friable form having an average effective particle size (e.g., such as slender needles and thin plates). Friable particles can be formed by selecting suitable solvents, surfactants or combination of surfactants, the temperature of the individual solutions, the rate of mixing and rate of precipitation and the like. Friability may also be enhanced by the introduction of lattice defects (e.g., cleavage planes) during the steps of mixing the first solution with the aqueous solvent. This would arise by rapid crystallization such as that afforded in the precipitation step. In the energy-addition step these friable crystals are converted to crystals that are kinetically stabilized and having an average effective particle size smaller than those of the presuspension. Kinetically stabilized means particles have a reduced tendency to aggregate when compared to particles that are not kinetically stabilized. In such instance the energy-addition step results in a breaking up of the friable particles. By ensuring the particles of the presuspension are in a friable state, the organic compound can more easily and more quickly be prepared into a particle within the desired size ranges when compared to processing an organic compound where the steps have not been taken to render it in a friable form.

D. Fourth Process Category

The methods of the fourth process category include the steps of the first process category except that the mixing step is carried out simultaneously with the energy-addition step.

E. Polymorph Control

The present process further provides additional steps for controlling the crystal structure of an organic compound to ultimately produce a suspension of the compound in the desired size range and a desired crystal structure. What is meant by the term "crystal structure" is the arrangement of the atoms within the unit cell of the crystal. Compounds that can be crystallized into different crystal structures are said to be polymorphic. Identification of polymorphs is important step in drug formulation since different polymorphs of the same drug can show differences in solubility, therapeutic activity, bioavailability, and suspension stability. Accordingly, it is important to control the polymorphic form of the compound for ensuring product purity and batch-to-batch reproducibility.

The steps to control the polymorphic form of the compound includes seeding the first solution, the second solvent or the pre-suspension to ensure the formation of the desired polymorph. Seeding includes using a seed compound or adding energy. In a preferred form the seed compound is a pharmaceutically-active compound in the desired polymorphic form. Alternatively, the seed compound can also be an inert impurity, a compound unrelated in structure to the desired polymorph but with features that may lead to templating of a crystal nucleus, or an organic compound with a structure similar to that of the desired polymorph.

The seed compound can be precipitated from the first solution. This method includes the steps of adding the organic compound in sufficient quantity to exceed the solubility of the organic compound in the first solvent to create a supersaturated solution. The supersaturated solution is treated to precipitate the organic compound in the desired polymorphic form. Treating the supersaturated solution includes aging the solution for a time period until the formation of a crystal or crystals is observed to create a seeding mixture. It is also possible to add energy to the supersaturated solution to cause the organic compound to precipitate out of the solution in the desired polymorph. The energy can be added in a variety of ways including the energy addition steps described above. Further energy can be added by heating, or by exposing the pre-suspension to electromagnetic energy, particle beam or electron beam sources. The electromagnetic energy includes light energy (ultraviolet, visible, or infrared) or coherent radiation such as that provided by a laser, microwave energy such as that provided by a maser (microwave amplification by stimulated emission of radiation), dynamic electromagnetic energy, or other radiation sources. It is further contemplated utilizing ultrasound, a static electric field, or a static magnetic field, or combinations of these, as the energy-addition source.

In a preferred form, the method for producing seed crystals from an aged supersaturated solution includes the steps of: (i) adding a quantity of an organic compound to the first organic solvent to create a supersaturated solution, (ii) aging the supersaturated solution to form detectable crystals to create a seeding mixture; and (iii) mixing the seeding mixture with the second solvent to precipitate the organic compound to create a pre-suspension. The presuspension can then be further processed as described in detail above to provide an aqueous suspension of the organic compound in the desired polymorph and in the desired size range.

Seeding can also be accomplished by adding energy to the first solution, the second solvent or the pre-suspension provided that the exposed liquid or liquids contain the organic compound or a seed material. The energy can be added in the same fashion as described above for the supersaturated solution.

Accordingly, the present processes utilize a composition of matter of an organic compound in a desired polymorphic form essentially free of the unspecified polymorph or polymorphs. In a preferred form, the organic compound is a pharmaceutically active substance. It is contemplated the methods described herein can be used to selectively produce a desired polymorph for numerous pharmaceutically active compounds.

The first process category, as well as the second, third, and fourth process categories, can be further divided into two subcategories, Method A and B.

The first solvent according to the following processes is a solvent or mixture of solvents in which the organic compound of interest is relatively soluble and which is miscible with the second solvent. Such solvents include, but are not limited to water-miscible protic compounds, in which a hydrogen atom in the molecule is bound to an electronegative atom such as oxygen, nitrogen, or other Group VA, VIA and VII A in the Periodic Table of elements. Examples of such solvents include, but are not limited to, alcohols, amines (primary or secondary), oximes, hydroxamic acids, carboxylic acids, sulfonic acids, phosphonic acids, phosphoric acids, amides and ureas.

Other examples of the first solvent also include aprotic organic solvents. Some of these aprotic solvents can form hydrogen bonds with water, but can only act as proton acceptors because they lack effective proton donating groups. One class of aprotic solvents is a dipolar aprotic solvent, as defined by the International Union of Pure and Applied Chemistry (IUPAC Compendium of Chemical Terminology, 2nd Ed., 1997):

A solvent with a comparatively high relative permittivity (or dielectric constant), greater than ca. 15, and a sizable permanent dipole moment, that cannot donate suitably labile hydrogen atoms to form strong hydrogen bonds, e.g. dimethyl sulfoxide.

Dipolar aprotic solvents can be selected from the group consisting of: amides (fully substituted, with nitrogen lacking attached hydrogen atoms), ureas (fully substituted, with no hydrogen atoms attached to nitrogen), ethers, cyclic ethers, nitriles, ketones, sulfones, sulfoxides, fully substituted phosphates, phosphonate esters, phosphoramides, nitro compounds, and the like. Dimethylsulfoxide (DMSO), N-methyl-2-pyrrolidinone (NMP), 2-pyrrolidinone, 1,3-dimethylimidazolidinone (DMI), dimethylacetamide (DMA), dimethylformamide (DMF), dioxane, acetone, tetrahydrofuran (THF), tetramethylenesulfone (sulfolane), acetonitrile, and hexamethylphosphoramide (HMPA), nitromethane, among others, are members of this class.

Solvents may also be chosen that are generally water-immiscible, but have sufficient water solubility at low volumes (less than 10%) to act as a water-miscible first solvent at these reduced volumes. Examples include aromatic hydrocarbons, alkenes, alkanes, and halogenated aromatics, halogenated alkenes and halogenated alkanes. Aromatics include, but are not limited to, benzene (substituted or unsubstituted), and monocyclic or polycyclic arenes. Examples of substituted benzenes include, but are not limited to, xylenes (ortho, meta, or para), and toluene. Examples of alkanes include but are not limited to, hexane, neopentane, heptane, isooctane, and cyclohexane. Examples of halogenated aromatics include, but are not restricted to, chlorobenzene, bromobenzene, and chlorotoluene. Examples of halogenated alkanes and alkenes include, but are not restricted to, trichloroethane, methylene chloride, ethylenedichloride (EDC), and the like.

Examples of the all of the above solvent classes include but are not limited to: N-methyl-2-pyrrolidinone (also called N-methyl-2-pyrrolidone), 2-pyrrolidinone (also called 2-pyrrolidone), 1,3-dimethyl-2-imidazolidinone (DMI), dimethylsulfoxide, dimethylacetamide, acetic acid, lactic acid, methanol, ethanol, isopropanol, 3-pentanol, n-propanol, benzyl alcohol, glycerol, butylene glycol (butanediol), ethylene glycol, propylene glycol, mono- and diacylated monoglycerides (such as glyceryl caprylate), dimethyl isosorbide, acetone, dimethylsulfone, dimethylformamide, 1,4-dioxane, tetramethylenesulfone (sulfolane), acetonitrile, nitromethane, tetramethylurea, hexamethylphosphoramide (HMPA), tetrahydrofuran (THF), dioxane, diethylether, tert-butylmethyl ether (TBME), aromatic hydrocarbons, alkenes, alkanes, halogenated aromatics, halogenated alkenes, halogenated alkanes, xylene, toluene, benzene, substituted benzene, ethyl acetate, methyl acetate, butyl acetate, chlorobenzene, bromobenzene, chlorotoluene, trichloroethane, methylene chloride, ethylenedichloride (EDC), hexane, neopentane, heptane, isooctane, cyclohexane, polyethylene glycol (PEG, for example, PEG-4, PEG-8, PEG-9, PEG-12, PEG-14, PEG-16, PEG-120, PEG-75, PEG-150), polyethylene glycol esters (examples such as PEG-4 dilaurate, PEG-20 dilaurate, PEG-6 isostearate, PEG-8 palmitostearate, PEG-150 palmitostearate), polyethylene glycol sorbitans (such as PEG-20 sorbitan isostearate), polyethylene glycol monoalkyl ethers (examples such as PEG-3 dimethyl ether, PEG-4 dimethyl ether), polypropylene glycol (PPG), polypropylene alginate, PPG-10 butanediol, PPG-10 methyl glucose ether, PPG-20 methyl glucose ether, PPG-15 stearyl ether, propylene glycol dicaprylate/dicaprate, propylene glycol laurate, and glycofurol (tetrahydrofurfuryl alcohol polyethylene glycol ether). A preferred first solvent is N-methyl-2-pyrrolidinone. Another preferred first solvent is lactic acid.

The second solvent is an aqueous solvent. This aqueous solvent may be water by itself. This solvent may also contain buffers, salts, one or more compounds of Formula 1, surfactant(s), water-soluble polymers, and combinations of these excipients.

Method A

In Method A, the organic compound (e.g., "drug") is first dissolved in the first solvent to create a first solution. The organic compound can be added from about 0.1% (w/v) to about 50% (w/v) depending on the solubility of the organic compound in the first solvent. Heating of the concentrate from about 30° C. to about 100° C. may be necessary to ensure total dissolution of the compound in the first solvent.

A second aqueous solvent is provided with and one or more compounds of Formula 1 and, optionally, one or more surfactants set forth below. Examples of surfactants that may be used in this Method A or any of the other methods for particle preparation in general, or those disclosed in the present patent application in particular, include anionic surfactants, cationic surfactants, zwitterionic surfactants, nonionic surfactants or a biologically surface active molecule added thereto. Suitable anionic surfactants include but are not limited to alkyl sulfonates, alkyl phosphates, alkyl phosphonates, potassium laurate, triethanolamine stearate, sodium lauryl sulfate, sodium dodecylsulfate, alkyl polyoxyethylene sulfates, sodium alginate, dioctyl sodium sulfosuccinate, phosphatidyl glycerol, phosphatidyl inosine, phosphatidylinositol, diphosphatidylglycerol, phosphatidylserine, phosphatidic acid and their salts, sodium carboxymethylcellulose, cholic acid and other bile acids (e.g., cholic acid, deoxycholic acid, glycocholic acid, taurocholic acid, glycodeoxycholic acid) and salts thereof (e.g., sodium deoxycholate, etc.).

Zwitterionic surfactants are electrically neutral but possess local positive and negative charges within the same molecule. Suitable zwitterionic surfactants include but are not limited to zwitterionic phospholipids. Suitable phospholipids include phosphatidylcholine, phosphatidylethanolamine, diacylglycero-phosphoethanolamine (such as dimyristoyl-glycero-phosphoethanolamine (DMPE), dipalmitoyl-glycero-phosphoethanolamine (DPPE), distearoyl-glycero-phosphoethanolamine (DSPE), and dioleolyl-glycero-phosphoethanolamine (DOPE)). Mixtures of phospholipids that include anionic and zwitterionic phospholipids may be employed in this invention. Such mixtures include but are not limited to lysophospholipids, egg or soybean phospholipid or any combination thereof. The phospholipid, whether anionic, zwitterionic or a mixture of phospholipids, may be salted or desalted, hydrogenated or partially hydrogenated or natural semisynthetic or synthetic. The phospholipid may also be conjugated with a water-soluble or hydrophilic polymer to specifically target the delivery to macrophages in the present invention. However, conjugated phospholipids may be used to target other cells or tissue in other applications. A preferred polymer is polyethylene glycol (PEG), which is also known as the monomethoxy polyethyleneglycol (mPEG). The molecule weights of the PEG can vary, for example, from 200 to 50,000. Some commonly used PEG's that are commercially available include PEG 350, PEG 550, PEG 750, PEG 1000, PEG 2000, PEG 3000, and PEG 5000. The phospholipid or the PEG-phospholipid conjugate may also incorporate a functional group that can covalently attach to a ligand including but not limited to proteins, peptides, carbohydrates, glycoproteins, antibodies, or pharmaceutically active agents. These functional groups may conjugate with the ligands through, for example, amide bond formation, disulfide or thioether formation, or biotin/streptavidin binding. Examples of the ligand-binding functional groups include but are not limited to hexanoylamine, dodecanylamine, 1,12-dodecanedicarboxylate, thioethanol, 4-(p-maleimidophenyl)butyramide (MPB), 4-(p-maleimidomethyl)cyclohexane-carboxamide (MCC), 3-(2-pyridyldithio)propionate (PDP), succinate, glutarate, dodecanoate, and biotin.

Suitable cationic surfactants include but are not limited to quaternary ammonium compounds, such as benzalkonium chloride, cetyltrimethylammonium bromide, chitosans, lauryldimethylbenzylammonium chloride, acyl carnitine hydrochlorides, dimethyldioctadecylammomium bromide (DDAB), dioleyoltrimethylammonium propane (DOTAP), dimyristoyltrimethylammonium propane (DMTAP), dimethylaminoethanecarbamoyl cholesterol (DC-Chol), 1,2-diacylglycero-3-(O-alkyl)phosphocholine, O-alkylphosphatidylcholine, alkyl pyridinium halides, or long-chain alkyl amines such as, for example, n-octylamine and oleylamine.

Suitable nonionic surfactants include: glyceryl esters, polyoxyethylene fatty alcohol ethers (Macrogol and Brij), polyoxyethylene sorbitan fatty acid esters (Polysorbates), polyoxyethylene fatty acid esters (Myrj), sorbitan esters (Span), glycerol monostearate, polyethylene glycols, polypropylene glycols, cetyl alcohol, cetostearyl alcohol, stearyl alcohol, aryl alkyl polyether alcohols, polyoxyethylene-polyoxypropylene copolymers (poloxamers), poloxamines, methylcellulose, hydroxymethylcellulose, hydroxypropylcellulose, hydroxypropylmethylcellulose, noncrystalline cellulose, polysaccharides including starch and starch derivatives such as hydroxyethylstarch (HES), polyvinyl alcohol, and polyvinylpyrrolidone. In a preferred form, the nonionic surfactant is a polyoxyethylene and polyoxypropylene copolymer and preferably a block copolymer of propylene glycol and ethylene glycol. Such polymers are sold under the trade name POLOXAMER also sometimes referred to as PLURONIC®, and sold by several suppliers including Spectrum Chemical and Ruger. Among polyoxyethylene fatty acid esters is included those having short alkyl chains. One example of such a surfactant is SOLUTOL® HS 15, polyethylene-660-hydroxystearate, manufactured by BASF Aktiengesellschaft. Surface-active biological molecules include such molecules as albumin, casein, hirudin or other appropriate proteins. Polysaccharide biologics are also included, and consist of but are not limited to, starches, heparins, and chitosans. Other suitable surfactants include any amino acids such as leucine, alanine, valine, isoleucine, lysine, aspartic acid, glutamic acid, methionine, phenylalanine, or any derivatives of these amino acids such as, for example, amide or ester derivatives and polypeptides formed from these amino acids.

It may also be desirable to add a pH adjusting agent to the second solvent. Suitable pH adjusting agents include, but are not limited to, hydrochloric acid, sulfuric acid, phosphoric acid, monocarboxylic acids (such as, for example, acetic acid and lactic acid), dicarboxylic acids (such as, for example, succinic acid), tricarboxylic acids (such as, for example, citric acid), THAM (tris(hydroxymethyl)aminomethane), meglumine (N-methylglucosamine), sodium hydroxide, and amino acids such as glycine, arginine, lysine, alanine, histidine and leucine. The second solvent should have a pH within the range of from about 3 to about 11. The aqueous medium may additionally include an osmotic pressure adjusting agent, such as but not limited to glycerin, a monosaccharide such as dextrose, a disaccharide such as sucrose, a trisaccharide such as raffinose, and sugar alcohols such as mannitol, xylitol and sorbitol.

In a preferred form, the method for preparing small particles of an organic compound includes the steps of adding the first solution to the second solvent. The addition rate is dependent on the batch size, and precipitation kinetics for the organic compound. Typically, for a small-scale laboratory process (preparation of 1 liter), the addition rate is from about 0.05 cc per minute to about 10 cc per minute. During the addition, the solutions should be under constant agitation. It has been observed using light microscopy that amorphous particles, semi-crystalline solids, or a supercooled liquid are formed to create a pre-suspension. The method further includes the step of subjecting the pre-suspension to an energy-addition step to convert the amorphous particles, supercooled liquid or semicrystalline solid to a more stable, crystalline solid state. The resulting particles will have an average effective particles size as measured by dynamic light scattering methods. In process category four, the first solution and the second solvent are combined while simultaneously conducting the energy-addition step.

The energy-addition step involves adding energy through sonication, homogenization, countercurrent flow homogenization, microfluidization, or other methods of providing impact, shear or cavitation forces. The sample may be cooled or heated during this stage. In one preferred form, the energy-addition step is effected by a piston gap homogenizer such as the one sold by Avestin Inc. under the product designation EmulsiFlex-C160. In another preferred form, the energy-addition step may be accomplished by ultrasonication using an ultrasonic processor such as the Vibra-Cell Ultrasonic Processor (600W), manufactured by Sonics and Materials, Inc. In yet another preferred form, the energy-addition step may be accomplished by use of an emulsification apparatus as described in U.S. Pat. No. 5,720,551 which is incorporated herein by reference and made a part hereof.

Depending upon the rate of energy addition, it may be desirable to adjust the temperature of the processed sample to within the range of from approximately −30° C. to 30° C. Alternatively, in order to effect a desired phase change in the processed solid, it may also be necessary to heat the pre-suspension to a temperature within the range of from about 30° C. to about 100° C. during the energy-addition step.

Method B

Method B differs from Method A in the following respects. The first difference is one or more compounds of Formula 1 and, optionally, one or more surfactant is added to the first solution. The surfactants may be selected from the groups of anionic, nonionic, cationic surfactants, and surface-active biological modifiers set forth above. A drug suspension resulting from application of the processes may be administered directly as an injectable solution, provided water for injection is used in formulation and an appropriate means for solution sterilization is applied. Sterilization may be accomplished by methods well known in the art such as steam or heat sterilization, gamma irradiation and the like. Other sterilization methods, especially for particles in which greater than 99% of the particles are less than 200 nm, would also include pre-filtration first through a 3.0 micron filter followed by filtration through a 0.45-micron particle filter, followed by steam or heat sterilization or sterile filtration through two redundant 0.2-micron membrane filters. Yet another means of sterilization is sterile filtration of the concentrate prepared from the first solvent containing drug and optional surfactant or surfactants and sterile filtration of the aqueous diluent. These are then combined in a sterile mixing container, preferably in an isolated, sterile environment. Mixing, homogenization, and further processing of the suspension are then carried out under aseptic conditions. Yet another procedure for sterilization would consist of heat sterilization or autoclaving within the homogenizer itself, before, during, or subsequent to the homogenization step. Processing after this heat treatment would be carried out under aseptic conditions.

Optionally, a solvent-free suspension may be produced by solvent removal after precipitation. This can be accomplished by centrifugation, dialysis, diafiltration, force-field fractionation, high-pressure filtration, reverse osmosis, or other separation techniques well known in the art. Complete removal of N-methyl-2-pyrrolidinone was typically carried out by one to three successive centrifugation runs; after each centrifugation (18,000 rpm for 30 minutes) the supernatant was decanted and discarded. A fresh volume of the suspension vehicle without the organic solvent was added to the remaining solids and the mixture was dispersed by homogenization. It will be recognized by those skilled in the art that other high-shear mixing techniques could be applied in this reconstitution step. Alternatively, the solvent-free particles can be formulated into various dosage forms as desired for a variety of administrative routes, such as oral, pulmonary, nasal, topical, intramuscular, and the like.

Furthermore, any undesired excipients such as surfactants may be replaced by a more desirable excipient by use of the separation methods described in the above paragraph. The solvent and first excipient may be discarded with the supernatant after centrifugation or filtration. A fresh volume of the suspension vehicle without the solvent and without the first excipient may then be added. Alternatively, a new surfactant may be added. For example, a suspension consisting of drug, N-methyl-2-pyrrolidinone (solvent), poloxamer 188 (first excipient), sodium deoxycholate, glycerol and water may be replaced with phospholipids (new surfactant), glycerol and water after centrifugation and removal of the supernatant.

Examples of particles of the present invention are illustrated in Examples 3 and 4:

EXAMPLE 3

Preparation of 1% Itraconazole Nanosuspension Using Poloxamer 188, Bis(4-Butanesulfonic Acid, Sodium Salt)

Figure 1:
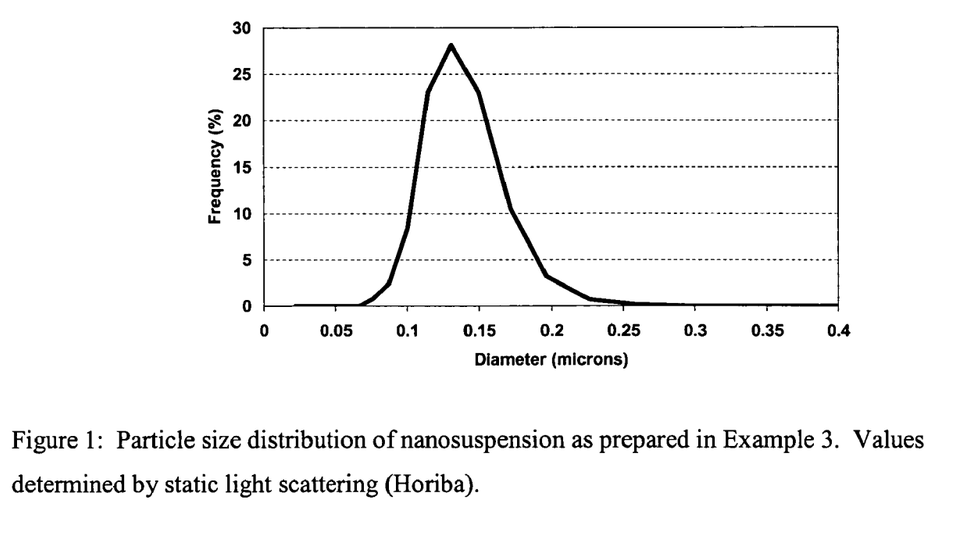
FIG. 1 illustrates the particle size distribution of a nanosuspension prepared in Example 1.

Solution A was prepared by dissolving 1 g itraconazole in 10 mL N-methyl-2-pyrrolidinone (NMP). An aqueous solution (80 mL) was prepared containing 100 mg of poloxamer 188, bis(4-butanesulfonic acid, sodium) and 2.2 g glycerin. This aqueous solution (Solution B) was adjusted to pH 8 with sodium hydroxide, and further diluted to a final solution volume of 100 mL. To a 25-mL Erlenmeyer flask was transferred 9 mL of solution B. With vigorous stirring, 1-mL of Solution A was added to Solution B. The resulting slurry was transferred to a piston-gap homogenizer (Avestin C5) and homogenized at 10,000 psi for 1 hour. After homogenization was complete, the suspension was placed in a 15-cc centrifuge tube and centrifuged for 30 minutes at 10,000 rpm, 25° C. The supernatant fluid was carefully decanted and discarded. Another 9 mL of Solution B was added, the pellet was broken up into a slurry using a glass rod, and the slurry was transferred to a vessel for a second homogenization. Residual solid was rinsed out of the tube with about 1 additional mL of Solution B and combined with the first portion. The slurry was homogenized, and centrifuged for 30 min at 10,000 rpm. The supernatant fluid was discarded, another fresh aliquot (9 mL) of Solution B was added, the pellet was broken up into a slurry with a glass rod, and the slurry was then homogenized. Particle distribution was assessed by static (Horiba) and dynamic (Malvern) light scattering. Particle size results (as measured by static light scattering) are shown in FIG. 1. Size distribution data acquired by dynamic light scattering are shown in Table 1.

Dynamic light scattering results (Malvern) are listed below:

TABLE 1

Dynamic light scattering results for nanosuspension as prepared in Example 3.

| | |
|---|---|
| Z-average size (nm): | 124 |
| Median (nm): | 150 |
| Diameter at 99% (nm): | 375 |
| Polydispersity index: | 0.152 |

EXAMPLE 4

Comparison of Stability of 1% Itraconazole Nanoparticles Prepared Using Poloxamer 188, Bis(4-Butanesulfonic Acid, Sodium Salt) with 1% Itraconazaole Nanoparticles Prepared Using Conventional Surfactant System (0.1% Poloxamer 188, 0.1% Sodium Deoxycholate)

Samples prepared by the method in Example 3 were stored at 5 and 40° C. in controlled-temperature chambers. Control samples were prepared by a similar procedure, however 0.1% (w/v) poloxamer 188, bis(4-butanesulfonic acid, sodium salt), was replaced with a mixture of 0.1% poloxamer 188 and the bile salt, 0.1% sodium deoxycholate. After one week, the particle size distributions (Horiba) of the control and experimental units were compared. These results are shown in Table 2.

Table 2 illustrates that 40° C. storage for one week induced particle growth in both control and experimental formulations. However, the stability of the experimental units that were prepared using the current invention are significantly more stable, as evidenced by the median, 90% and 99% cumulative particle distributions.

TABLE 2

Effect of storage at 40° C. on particle stability. Comparison between stability of 1% itraconazole nanosuspension prepared by application of the current invention versus that of a 1% itraconazole nanosuspension prepared using a conventional surfactant system (0.1% poloxamer 188, 0.1% sodium deoxycholate).

| | | Particle Size (nm) | | |
|---|---|---|---|---|
| Surfactant System | Storage | Median | 90% | 99% |
| Poloxamer 188, bis(4-butanesulfonic acid, sodium salt) (0.1%) | 5° C., 1 week | 126 | 161 | 195 |
| | 40° C., 1 week | 145 | 363 | 1218 |
| Poloxamer 188 (0.1%), sodium deoxycholate (0.1%) | 5° C., 1 week | 143 | 547 | 3204 |
| | 40° C., 1 week | 279 | 1512 | 3241 |

Figure 2:
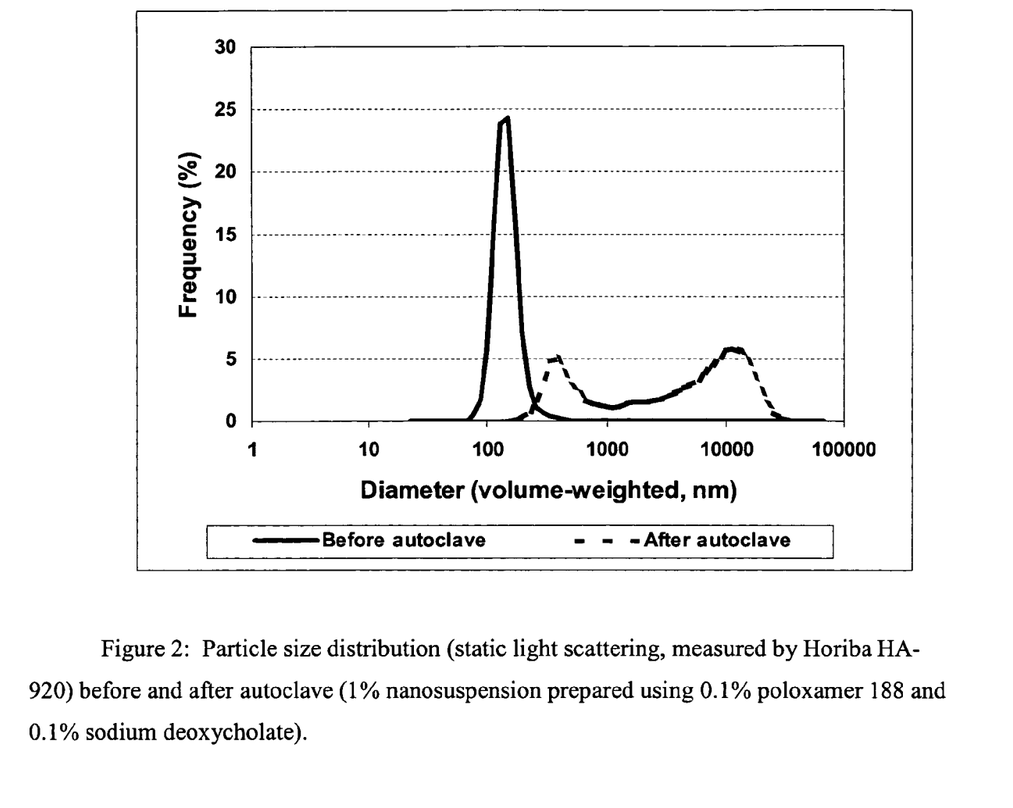
FIG. 2 illustrates the particle size distribution of nanosuspensions made with poloxamer 188 and sodium deoxycholate (Example 3).

Samples prepared by the method in Example 3 were autoclaved (AMSCO, Eagle Series 2022) using a total cycle time of 17 minutes (5 min hold @121 C, 6 min exhaust). Particle size distributions (Horiba LA-920) were monitored before and after sterilization, and are presented in FIGS. 2 and 3.

As is illustrated by the comparison of particle size distribution before and after autoclaving (FIG. 3), application of heat to the nanosuspension prepared using b 0.1% poloxamer 188 and 0.1% sodium deoxycholate led to extensive aggregation and particle growth. Before autoclave the median volume-weighted particle size, as measured by static light scattering, was about 132 nm, with a 99th percentile value of 276 nm. After autoclave, very significant broadening of the distribution occurred—the median volume-weighted particle size was 4.49 microns (4,490 nm), whereas the 99th percentile value for the particle distribution was about 23 microns (23,000 nm).

Figure 3:
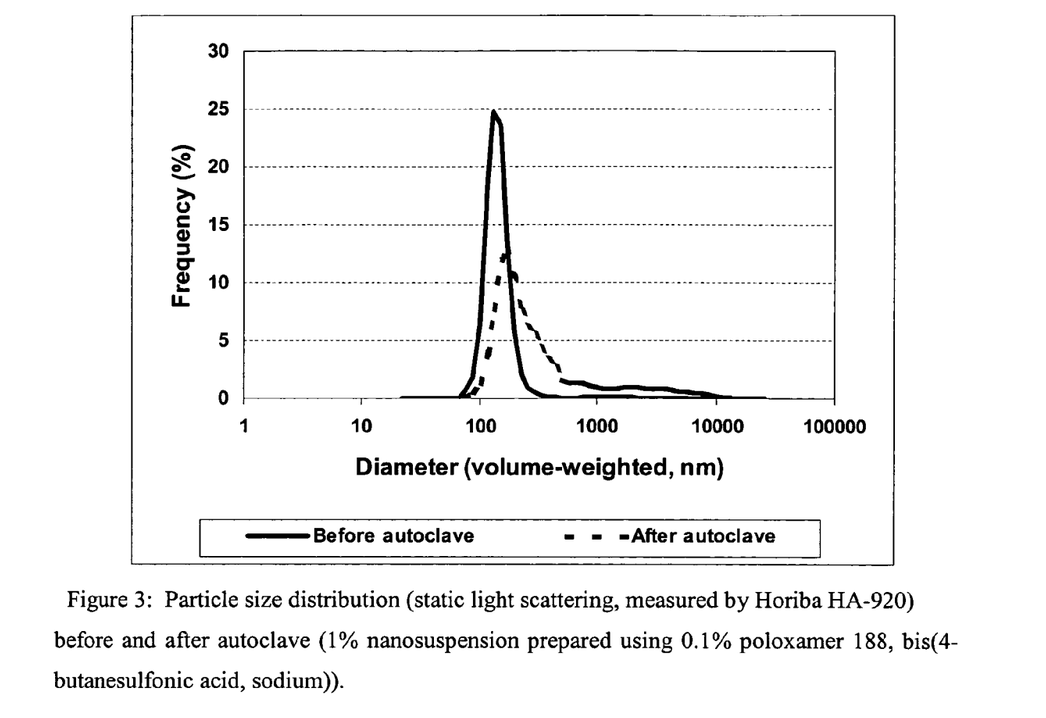
FIG. 3 illustrates the particle size distribution of a nanosuspension made with the compound, poloxamer 188, bis(4-butanesulfonic acid, sodium) (Example 3).

In contrast, application of heat energy to the 1% itraconazole nanosuspension prepared by use of this invention, poloxamer 188, bis(4-butanesulfonic acid, sodium), resulted in significantly less broadening of the particle distribution as shown in FIG. 3. Before autoclave, the median particle size measured by static light scattering was about 130 nm, and the 99th percentile value was about 732 nm. After sterilization, the median particle size after sterilization was about 202 nm, and the 99th percentile value was about 7.6 microns.

Under identical storage and autoclave conditions, the particle distribution results persuasively illustrate that use of the polymeric derivative disclosed in this invention, poloxamer 188, bis(4-butanesulfonic acid, sodium), in which both nonionic, multiple hydrophobic segments, and ionic moieties are built into the a single molecule, affords surprisingly greater stability than that attainable with conventional surface-active agents (poloxamer 188, and sodium deoxycholate), in which the polymer (poloxamer 188) likewise contains multiple hydrophobic segments, but does not contain ionic moieties within the same molecule.

While specific embodiments have been illustrated and described, numerous modifications come to mind without departing from the spirit of the invention and the scope of protection is only limited by the scope of the accompanying claims.

What is claimed is:

1. A compound of Formula 1:

Formula 1 wherein, x is an integer from 3 to 300;

y is an integer from 3 to 300;

z in an integer from 3 to 300;

$R_A$ and $R_B$ are, independently, a sulfonate of the following formula:

wherein R is an alkyl, cycloalkyl or aryl bridging group, and wherein $R_7$ is hydrogen or $R_7$ is absent such that the sulfonate is an anion, or mixtures thereof; provided, $R_1$, $R_2$, $R_3$, $R_4$, $R_5$, and $R_6$ are, independently, hydrogen, alkyl, or aryl groups, wherein the polymeric backbone is a triblock copolymer.

2. A compound of claim 1, wherein the polymeric backbone is a triblock copolymer of ethylene glycol and propylene glycol.

3. A compound of claim 1, wherein $R_1$, $R_2$, $R_3$, $R_5$, and $R_6$ are hydrogen, $R_4$ is $CH_3$ and wherein x is 80, y is 27 and z is 80, or x is 101, y is 56 and z is 101.

4. A compound of claim 1, wherein the substituent is butyl, propyl, pentyl, hexyl, heptyl, octyl, nonyl, decyl, undecyl, or dodecylsulfonic acid.

5. A compound of claim 4, wherein the substituent is n-butylsulfonic acid.

6. A compound of claim 1, having the formula:

wherein, x is from 50 to 120, y is from 20 to 60, and z is from 50 to 120; and R and R' are, independently, absent, hydrogen or a cation.

7. A compound of claim 6, wherein x is 80, y is 27 and z is 80, or x is 101, y is 56 and z is 101.

8. A compound of claim 6, having the formula:

wherein R and R' are, independently, absent, hydrogen or a cation, and mixtures thereof.

9. A compound of claim 6, having the formula:

wherein R and R' are, independently, absent, hydrogen or a cation, and mixtures thereof.

10. A composition comprising particles, said particles comprising a poorly water soluble compound, and a coating comprising one or more compounds of claim 1 adsorbed to said particles, wherein the poorly water soluble compound has a water solubility less than about 10 mg/mL.

11. A composition of claim 10, wherein the poorly water soluble compound is selected from the group consisting of therapeutic agents and diagnostic agents.

12. A composition of claim 10, wherein the polymeric backbone is a triblock copolymer of ethylene glycol and propylene glycol.

13. A composition of claim 10, wherein $R_1$, $R_2$, $R_3$, $R_5$, and $R_6$ are hydrogen, $R_4$ is $CH_3$ and wherein x is 80, y is 27 and z is 80, or x is 101, y is 56 and z is 101.

14. A composition of claim 10, wherein the substituent is butyl, propyl, pentyl, hexyl, heptyl, octyl, nonyl, decyl, undecyl, or dodecylsulfonic acid.

15. A composition of claim 14, wherein the substituent is n-butylsulfonic acid.

16. A composition of claim 10, wherein the compound is of the formula:

wherein, x is from 50 to 120, y is from 20 to 60, and z is from 50 to 120; and R and R' are, independently, absent, hydrogen or a cation.

17. A composition of claim 16, wherein x is 80, y is 27 and z is 80, or x is 101, y is 56 and z is 101.

18. A composition of claim 10, wherein the compound is:

wherein R and R' are, independently, absent, hydrogen or a cation, and mixtures thereof.

19. A composition of claim 10, wherein the compound is:

wherein R and R' are, independently, absent, hydrogen or a cation, and mixtures thereof.

20. A composition of claim 10, wherein the average effective particle size of the particles is between 15 nm and 200 microns.

21. A composition of claim 20, wherein the particle size is between 15 nm and 100 microns.

22. A composition of claim 10, wherein the compound(s) of claim 1 are present in an amount effective to maintain an average effective particle size between 15 nm and 100 microns.

23. A composition of claim 22, wherein the particle size is between 15 nm and 50 microns.

24. A method of synthesizing a compound of claim 1, comprising reacting a polyalkylene glycol in the presence of a sultone or a substituted alkylsulfonic acid.

25. A method of claim 24, wherein the sultone is of formula 2

Formula 2 and wherein n is 1 to 6.

26. A method of claim 24, wherein the substituted alkylsulfonic acid is of formula 3:

Formula 3 and wherein n is 1 to 20, and X is selected from the group consisting of Cl, Br, I, mesylate, tosylate and triflate.

27. A method of making the compound of claim 8, comprising reacting with 1,4 butane sultone.

* * * * *